(12) United States Patent
Bond et al.

(10) Patent No.: US 6,786,096 B2
(45) Date of Patent: Sep. 7, 2004

(54) SYSTEM AND TECHNIQUE FOR DETECTING THE PRESENCE OF FOREIGN MATERIAL

(75) Inventors: Leonard J. Bond, Richland, WA (US); Aaron A. Diaz, West Richland, WA (US); Richard A. Pappas, Richland, WA (US); Timothy Stewart, Pendleton, OR (US)

(73) Assignee: Battelle Memorial Institute, Richland, WA (US)

(*) Notice: Subject to any disclaimer, the term of this patent is extended or adjusted under 35 U.S.C. 154(b) by 50 days.

(21) Appl. No.: 10/000,263

(22) Filed: Nov. 28, 2001

(65) Prior Publication Data

US 2003/0098796 A1 May 29, 2003

(51) Int. Cl.[7] ............................................. G01N 29/04
(52) U.S. Cl. ........................................... 73/598; 73/600
(58) Field of Search ........................ 73/579, 596, 597, 73/598, 599, 600, 602, 590, 618, 620, 624, 625, 627, 628, 629, 630

(56) References Cited

U.S. PATENT DOCUMENTS

| | | | |
|---|---|---|---|
| 4,208,915 A | 6/1980 | Edwards ...................... 73/620 |
| 4,214,484 A | 7/1980 | Abts | |
| 4,217,781 A | 8/1980 | Abts | |
| 4,226,540 A | 10/1980 | Barten et al. ................ 356/445 |
| 4,339,944 A | 7/1982 | Abts et al. | |
| 4,384,476 A | 5/1983 | Black et al. ................... 73/61 |
| 4,527,420 A | 7/1985 | Foote ........................... 73/61 |
| 4,542,644 A | 9/1985 | Claytor et al. ................ 73/61 |
| 4,735,097 A | 4/1988 | Lynnworth ............... 73/861.28 |
| 4,821,573 A | 4/1989 | Nagata et al. ................ 73/597 |
| 4,894,201 A | 1/1990 | Ahmed ....................... 376/261 |
| 4,978,225 A | 12/1990 | Reimer ....................... 356/432 |
| 5,059,031 A | 10/1991 | Hamel et al. ............... 356/428 |
| 5,062,299 A | 11/1991 | Davis et al. .................. 73/609 |
| 5,241,365 A | 8/1993 | Haagensen .................. 356/376 |
| 5,291,773 A | 3/1994 | Kamon ...................... 73/24.03 |
| 5,351,560 A | 10/1994 | Russwurm ............... 73/861.27 |
| 5,504,572 A | 4/1996 | Taylor et al. ................. 356/53 |
| 5,641,907 A | 6/1997 | Haagensen .................. 73/620 |
| 5,684,252 A | 11/1997 | Kessler et al. ............... 73/618 |
| 5,723,773 A | 3/1998 | Bryan ....................... 73/61.75 |
| 5,745,228 A | 4/1998 | Hebrank et al. .............. 356/53 |

(List continued on next page.)

FOREIGN PATENT DOCUMENTS

| | | | |
|---|---|---|---|
| EP | 1 092 976 A2 | 9/2000 | ....................... 29/2 |
| JP | 4-166063 | * 6/1992 | |

OTHER PUBLICATIONS

Goebbels, K., "Structure Analysis by Scattered Ultrasonic Radiation", Research Technology in NDT, vol. 4, Chapter 4, Shafe. Academic Press.

Proceedings of the 16th International Congress on Acoustics and the 135th Meeting of the Acoustical Society of American, Jun. 20–26, 1998, Seattle, WA.

Bond, L.J. and Saffari, N, "Mode–conversion Ultrasonic Testing", Chapter 5; Nondestructive Testing, vol. 7, pp. 146–189, ISBN 0–12–639057–6, 1984, Academic Press, London.

Lawrie, W.E., "Ultrasonic Nondestructive Coating Evaluation", AF Conference Proceedings, pp. 343–371 (1964).

Primary Examiner—Helen Kwok
(74) Attorney, Agent, or Firm—Woodard, Emhardt, Moriarty, McNett & Henry LLP (57) ABSTRACT

A system and technique for detecting the presence of foreign material is presented. An ultrasound transmitter interrogates the bulk material and an array of detectors receives the off angle ultrasound scattering response of the bulk material. The presence of foreign material is determined when the off angle scattering response exceeds a predetermined threshold. The technique is especially suitable for the detection of bone in meat.

58 Claims, 9 Drawing Sheets

U.S. PATENT DOCUMENTS

| | | | |
|---|---|---|---|
| 5,847,382 A | 12/1998 | Koch et al. | 250/223 |
| 5,981,892 A | 11/1999 | Baird et al. | 209/590 |
| 6,061,086 A | 5/2000 | Reimer et al. | 348/125 |
| 6,167,759 B1 | 1/2001 | Bond et al. | 73/602 |
| 6,176,132 B1 | 1/2001 | MacLauchlan | 73/290 |
| 6,324,901 B1 | 12/2001 | Fluh et al. | |
| 6,401,538 B1 | 6/2002 | Han et al. | 73/599 |

\* cited by examiner

SYSTEM AND TECHNIQUE FOR DETECTING THE PRESENCE OF FOREIGN MATERIAL

BACKGROUND

The present invention is directed to the detection of foreign material. More particularly, but not exclusively, it is directed to the detection of foreign material in heterogeneous process streams such as process streams of foodstuffs. In one particular application the invention is directed to the detection of bone in a slurry of chicken meat.

During manufacturing or processing, the presence of foreign material is a persistent problem. Foreign material is sometimes accidentally introduced into a process stream, for example when small objects or contaminates fall into a process stream. Foreign material also occurs more naturally, such as when components of the raw materials are separated or otherwise processed and one type of component is inadequately removed. Examples of this latter type are prevalent in the food processing area, and include the undesirable presence of bone, pits, seeds, cores, or any other similar objects either in whole or fragmentary form in a stream of foodstuffs. Regardless of the foreign object source, it is generally desirable to detect and/or remove any foreign material to assure the quality and safety of the resulting product.

It is therefore an object of the present invention to provide a system and technique for detecting foreign material. Further, because traditionally it is more difficult to differentiate between foreign material and heterogeneous bulk material, it is a further object to provide systems and techniques that are operable to detect foreign material in an otherwise heterogeneous material. It is also an object to provide systems and techniques operable to detect foreign material in a process stream and to remove the foreign material from the process stream. It is a further object to provide systems and techniques that can reliably detect foreign material in a rapid and cost effective manner. It is a still further object to provide a novel method for the determination of other properties of a materials, such as the characterization of the degree of mixing or inhomogeneity in an inhomogenerous system. One or more of these or other objects are met by various embodiments of the present invention.

SUMMARY

The present invention provides novel systems and techniques for detecting the presence of foreign material by detecting an off-angle ultrasound scattering response. In one embodiment, a process stream is interrogated with pulses of a focused sound field spanning a portion of the stream. The off-angle scattering response to the interrogating is then detected with a plurality of spaced receivers, with the presence of foreign material determined from the received response. In one refinement, the ultrasound receivers are focused on different sections of the insonified field and provide an indication of the relative location of detected foreign material in the process stream.

Another embodiment of the invention provides a novel technique for the detection of foreign material in a product including interrogating the product with ultrasound and determining the presence of foreign material based on the detected off-angle ultrasound scattering response. In further refined embodiments, the detected scattering response is compared to a threshold to determine the presence of foreign material. In other embodiments, the detected response from a plurality of off-angle detectors are used to determine the presence of foreign material. In still further refined embodiments, the inventive technique is used to detect foreign material in flowing inhomogeneous process slurries, and/or the technique is used to detect foreign material in foodstuffs.

There is also provided a novel system for detecting a property of a process stream. The system includes a conveyor operable to provide a process stream, an inspection device operable to measure an off-angle ultrasound scattering response of the process stream, and a processing device operable to determine a property of the material from the measured off-angle scattering response. In refined embodiments, the interrogation device is operable to transmit ultrasound to interrogate the process stream and is operable to receive an off-angle ultrasound scattering response to the interrogation with ultrasound. In further refinements, the processing device is operable to determine presence of foreign material in the process stream based on a comparison of the off-angle ultrasound scattering response to a predetermined threshold. In still further refinements, the inspection device includes a plurality of ultrasound receivers aligned non-parallel to at least one ultrasound transmitter.

Also provided is a novel method of determining a property of an inhomogeneous fluid, two phase system (solid in fluid or a fluid-fluid emulsion), and/or slurry. This novel method comprises interrogating the fluid with ultrasound, detecting an off-angle ultrasound scattering response, and determining a property of the fluid based on the off-angle ultrasound scattering response. In particular embodiments, the determined property can be, for example, one or more of the foreign material content, the degree of mixing, or the degree of inhomogeneity of the fluid. In further refined embodiments, the detected off angle scattering response scatters at an angle between about 10° and 45°, or more preferably between 15° and 30° of an interrogation axis. In still further refined embodiments the method includes detecting the off-angle scattering response from a plurality of receivers spaced around an interrogation axis, the property of the fluid determined from the response from the plurality of receivers. Properties of the system determinable by this or other embodiments include the degree of mixing, degree of inhomogeneity, or consistency of a system.

Also provided is a novel system including a conduit defining a flow path with a generally rectangular cross section, one or more inspection devices operable to transmit ultrasound to interrogate a process stream in the generally rectangular portion of the flow path, a plurality of spaced receivers each operable to receive an off-angle ultrasound scattering response to interrogation with the ultrasound; and a processing device operable to determine presence of a foreign material in the process stream based on a comparison of the off-angle ultrasound scattering response to a predetermined threshold.

Also provided is a novel system comprising a conduit operable to receive a process stream, one or more inspection devices operable to interrogate a volume of material in the process stream with ultrasound, at least two receivers focused on substantially non-overlapping interrogated volumes of material each operable to receive an off-angle ultrasound scattering response to the interrogation; and a processing device operable to determine presence of a foreign material in the process stream and to provide an indication of the spatial location of the foreign material in the process stream based on a comparison of the off-angle ultrasound scattering response of each receiver to a predetermined threshold.

DESCRIPTION OF PREFERRED EMBODIMENTS

For the purposes of promoting an understanding of the principles of the invention reference will now be made to the embodiments illustrated in the drawings and specific language will be used to describe the same. It will nevertheless be understood that no limitation of the scope of the invention is thereby intended. Any alterations and further modifications in the illustrated embodiments, and any further applications of the principles of the invention as illustrated herein are contemplated as would normally occur to one skilled in the art to which the invention relates.

Figure 1:
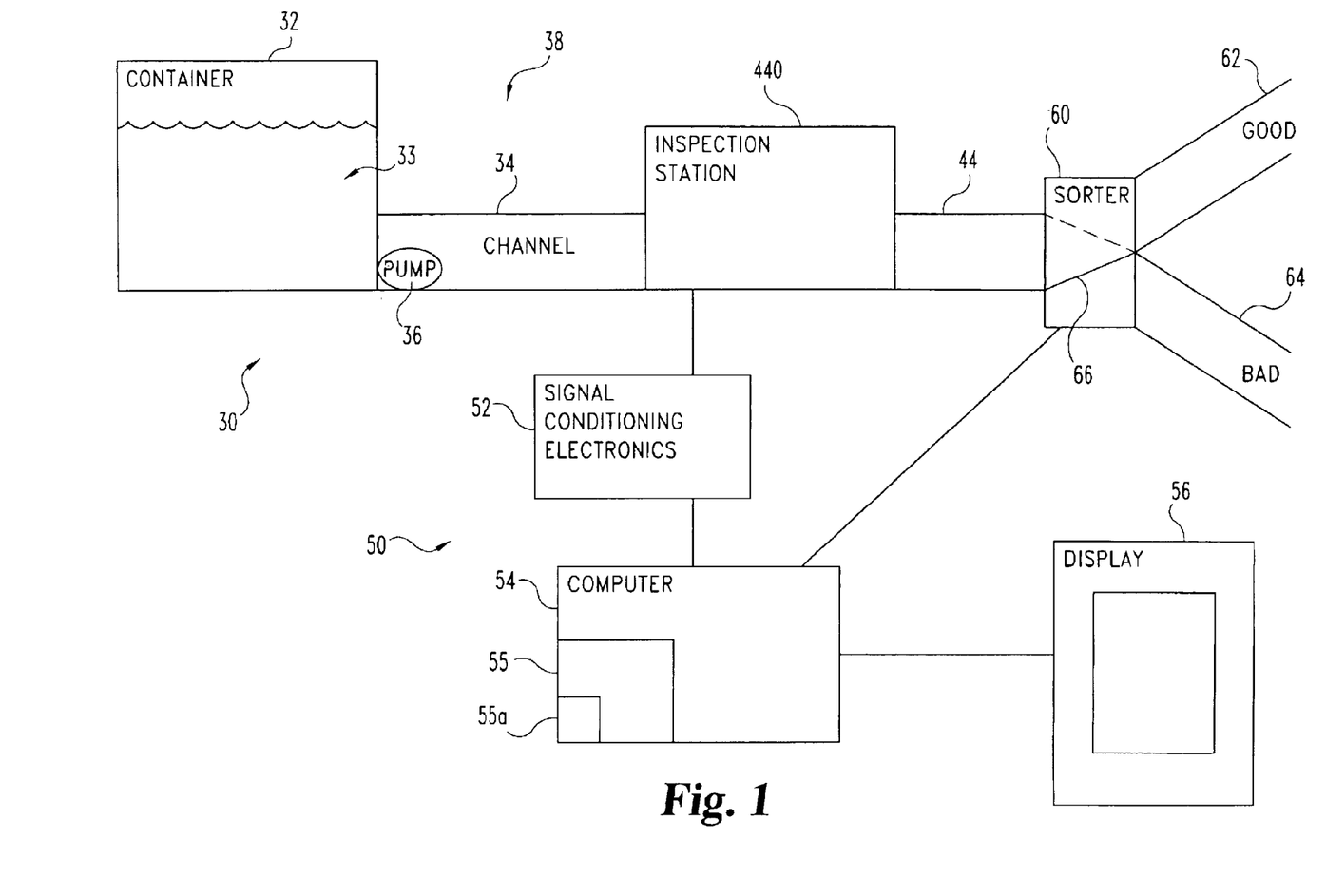
FIG. 1 is a schematic illustration of a processing system according to an embodiment of the present invention.

Turning now to FIG. 1 a processing system 30 for determining the presence of foreign material is depicted. System 30 includes a material supply container 32, an inspection station 440, and a sorting station 60. System 30 also includes a conveyor assembly 38 for transporting the bulk process material 33 from container 32, through inspection station 440 to sorting station 60. System 30 is adapted to interrogate a bulk fluid material, and conveyor assembly 38 includes channel 34 and pump 36 operative to pump material 33 through inspection station 440 and to sorting station 60 via channel 44.

At inspection station 440, the bulk material 33 is interrogated with ultrasound. The bulk material 33 interacts with the ultrasound and in response to the interaction scatters ultrasound in all directions. A portion of this scattered ultrasound (the scattering response) is detected by ultrasound receivers. Station 440 is electrically connected to processing assembly 50, which includes signal conditioning electronics 52, computer 54, and display 56. Assembly 50 receives a signal representative of the scattering response and determines the presence of foreign material in bulk process material 33 based on the received scattering response. Assembly 50 also is connected to sorting station 60 for operation of diversion valve 66. Valve 66 normally directs the bulk material 33 down channel 62. However, when bulk material 33 is determined to contain foreign material, valve 66 is operated to direct at least a portion of the bulk material 33 containing the foreign material down channel 64.

Figure 8A:
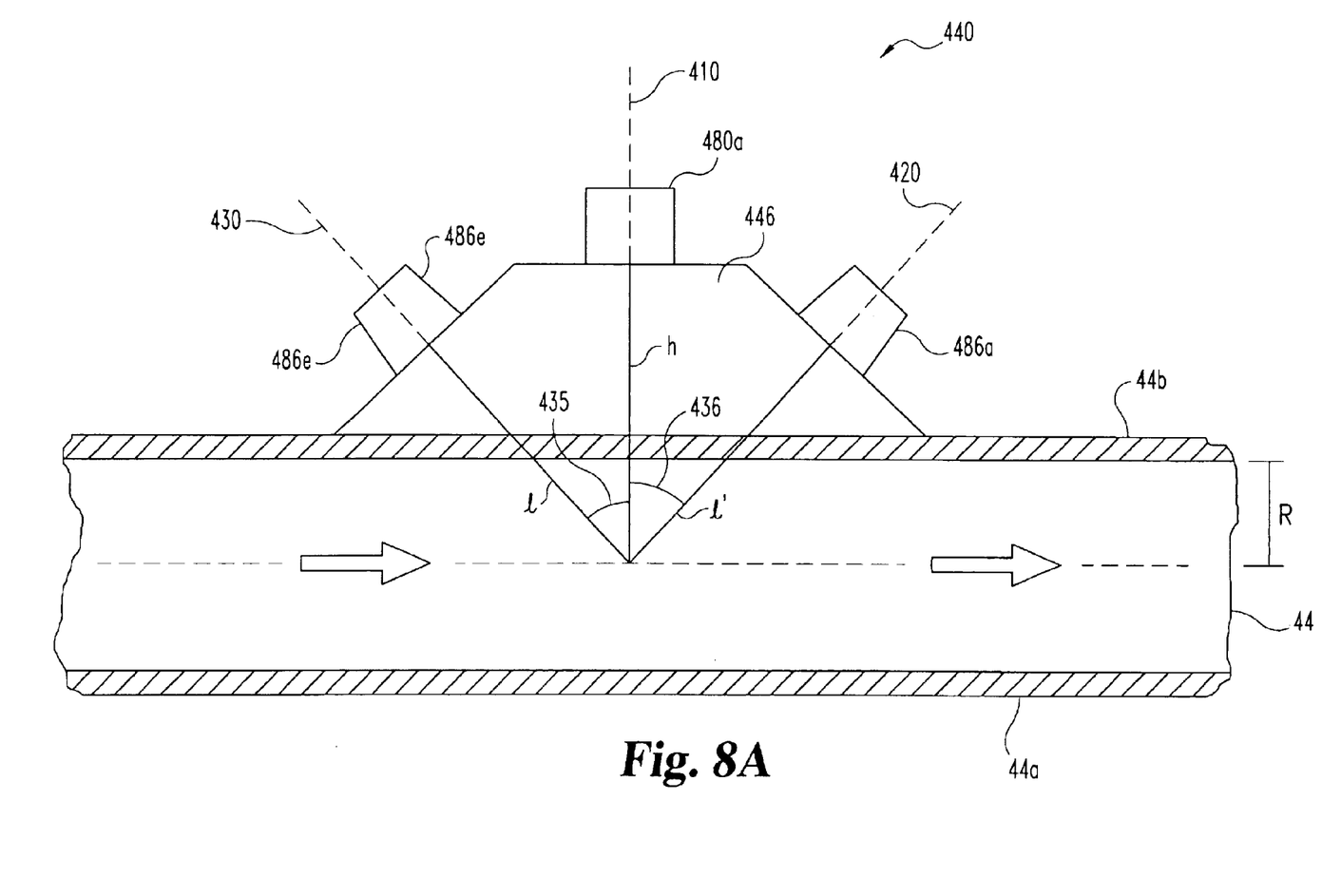
FIGS. 8A and 8B are side and top views respectively of the inspection station utilized to perform the experimental example described hereinafter.
Figure 8B:
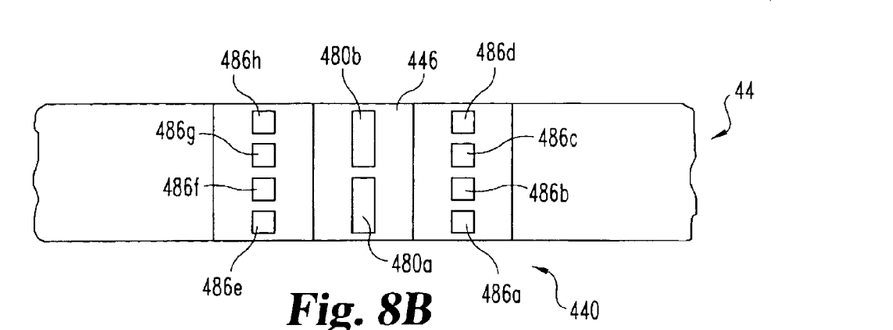

Turning now to FIGS. 8A and 8B, more particular features of inspection station 440 are illustrated. Station 440 includes a pair of ultrasound transmitters 480a and 480b and a plurality of ultrasound receivers 486a–486h. Transmitters 480a and 480b are mounted to the upper surface of solid wedge piece 446 and aligned parallel to interrogation axis 410 perpendicular to the flow direction. Receivers 486a–486h are mounted to the angled sides of wedge piece 446 and are aligned parallel to detection axes 420 and 430. Wedge piece 446 serves as a solid acoustic couplant between the ultrasound inspection devices and the process stream.

Channel 44 is rectangular in cross section, and both wedge piece 446 and upper wall 44b of channel 44 are of uniform thickness across the width of channel 44, providing a generally uniform acoustic pathlength for sound coupled into and out of channel 44. Preferably, both wedge piece 446 and wall 44b of channel 44 are formed of the same solid material such as stainless steel, Plexiglas, or Lucite. Piece 446 and wall 44b together form an acoustic path for ultrasound to travel from transmitters 480a and 480b to the contents of channel 44, and also for the scattering response to travel from channel 44 to receivers 486a–486h. In a preferred embodiment, wedge piece 446 is integral with upper wall 44b, where it is to be understood that the integral unit can be formed by machining or molding the components as a unitary structure. In alternative embodiments, wedge piece 446 is bolted, glued, or otherwise affixed to wall 44b.

Figure 9A:
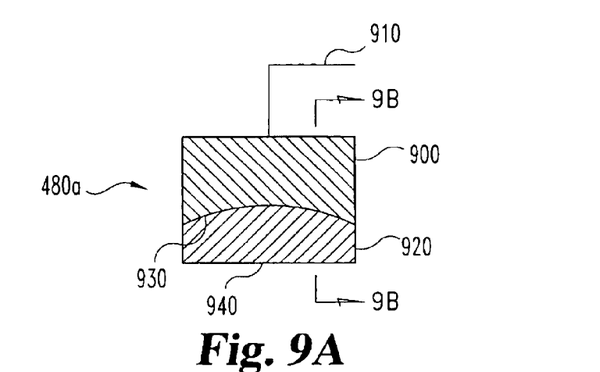
FIGS. 9A and 9B are side sectional views of a cylindrically focused inspection device.
Figure 9B:
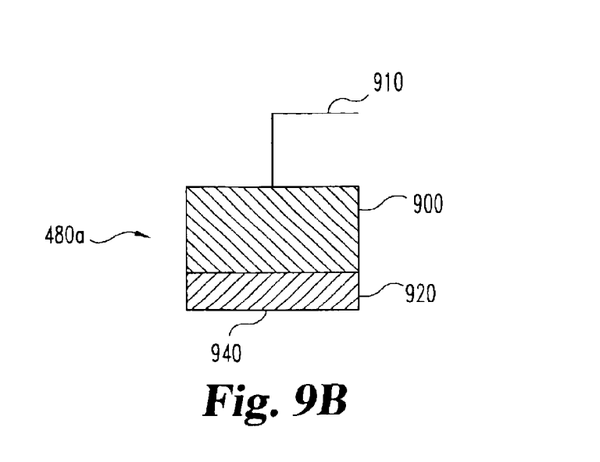

Each of the transmitters 480a and 480b are elongated and placed end-to-ent to generally span the width of channel 44. Transmitters 480a and 480b are also each cylindrically focused. In operation, transmitters 480a and 480b produce a focused sound field in channel 44. As shown in FIGS. 9A and 9B, transmitter 480a includes an ultrasonic transducer 900 with signal line 910. Transducer 900 has a cylindrically concave face 930 configured to produce a cylindrically focused sound field. A correspondingly convex acoustic coupling 920 and/or delay material is provided in contact with the concave face 930 of the transducer 900 so as to provide a transducer assembly with a generally flat outer surface 940 for placement adjacent the flat outer surface of wedge piece 446. It is also contemplated that wedge piece 446 could include a correspondingly convex surface with coupling 920 omitted. Alternatively or in addition, other acoustic coupling materials, such as a gel, could be provided between transducer 900 and piece 446 to form the desired acoustic transmission paths. In one alternative embodiment, a single transmitter is used in place of the two transducer arrangement. In another alternative embodiment, transmitters 480a and 480b are placed in a staggered, rather than end-to-end, orientation.

The receivers 486a–486h are also each cylindrically focused and can be configured similar to transmitter 480a. Another example of a cylindrically focused transducer assembly useful in the present invention is given in U.S. Pat. No. 5,062,299 to Davis et al. which is hereby incorporated by reference in its entirety. In addition or as an alternative to cylindrically focused transducer assemblies, spherically focused assemblies may be used as one or more of the transmitters (480a or 480b) and/or receivers (486a–486h). In still other embodiments, phased arrays of transducers could be used to create the desired focused acoustic sound field.

In operation, transmitters 480a and 480b are simultaneous pulsed to form a focused acoustic sound field in channel 44.

Signal conditioning electronics 52 (see FIG. 1) receive the response from the ultrasound receivers 486a–486h and include a time gate to select that portion of the signal representing the scattering response from material in channel 44. The gating parameters can be empirically determined by observing the scattered signal on an oscilloscope and selecting the portion of the signal between the reflections from the inside surfaces of upper and lower channel walls 44b and 44a respectively. Electronics 52 include an analog-to-digital converter to digitize the signal and pass the digitized scattering response to computer 54. Computer 54 contains memory 55 and transportable memory device 55a, such as an optical or electromagnetic disk, and includes programming instructions operable to cause computer 54 to process the scattering response in real time and determine the presence of foreign material based on that processed response.

In one embodiment of this processing, the presence of foreign material is determined by comparing off angle scattering response from the material in the inspection zone to an amplitude threshold set based on the response from "uncontaminated" material. If the scattering response signal exceeds this threshold, the suspected presence of a foreign material is determined. Alternatively, this comparison could be performed using analog signal processing techniques.

In one form, the scattering response from each of the plurality of receivers 486a–486h is provided to computer 54 through multiple, parallel signal channels. A background noise signal can be determined by averaging these signals over several clean runs of the bulk material without any foreign material in the stream. Alternatively, a background noise signal can be determined by maintaining a rolling average signal template of these signals under operating conditions, where the rolling average window is long enough to minimize any effects due to the infrequent occurrence of foreign material. Computer 54 then subtracts the background noise component from the received response. A separate background signal can be determined for each receiver 486a–486h to account for variations between receivers 486a–486h. After subtracting the background signal, computer 54 determines the maximum magnitude of the resulting signal and compares that maximum value to a threshold set for the associated receivers 486a–486h to determine the presence of foreign material.

In one preferred form, adaptive signal processing in used. In this form the background signal is a rolling average signal template determined under operating conditions. This rolling average signal will reflect changes in the operating conditions, such as changes in the temperature, composition, consistency, or degree of mixing of the bulk material. In one embodiment, changes in this rolling average signal are quantified and used to indicate corresponding changes in the composition or consistency of the bulk fluid either alone or in combination with foreign material detection.

In another embodiment, the scattering response is compared to entries in a library of different scattering responses for similar material of known content. In this manner, characteristics of the process stream can be determined when a detected scattering response matches one in the library. Other approaches may also be employed such as comparison of the received response to a scattering model and/or use of a neural network to recognize features in the scattering response.

Once the suspected presence of foreign material is determined with computer 54, computer 54 (or a different controller) provides a corresponding indication on display 56 and sets a detection flag. Optionally, the location of the foreign material in the process stream can be indicated. Computer 54 generates one or more control signals to operate diversion valve 66 to divert the contaminated product from the stream, calculating the appropriate travel time from inspection station 440 to valve 66. It is to be understood that integrated circuit microcontrollers or one or more programmable logic controllers (PLCs) can be used in place of computer 54.

In a particular embodiment, sets of receivers 486a–486h are focused on overlapping insonified volumes of material in the channel 44. For example, in FIG. 8A receivers 486a and 486e are focused on overlapping volumes. The scattering response of each of multiple receivers 486a–486h to the same interrogation pulse can then be compared to associated thresholds for each of the multiple receivers 486a–486h. When a predetermined number of receivers focused on overlapping volumes produce a response to the interrogation pulse exceeding the predetermined threshold, for example 2 of such receivers, foreign material is determined to be present. By employing multiple receivers trained on overlapping volumes, the occurrence of false positives can be reduced and/or the sensitivity of each receiver can be increased, for example by reducing the threshold for that receiver.

It should also be understood that certain different receivers can be arranged to focus on substantially different volumes. For example, as shown in FIG. 8B receivers 486a and 486h are focused on non-overlapping parts of channel 44. By examining the response from these non-overlapping receivers, the relative location of foreign material in stream 44 can often be determined with greater resolution, facilitating diversion of a relatively smaller portion of the process stream.

While not intending to be bound by any theory of operation, the off-angle scattering response differentiates between scattering targets in the bulk process stream and the foreign material to be detected because of contrast between acoustic impedance, particle size and/or shape verses that for the background matrix of the bulk material. Scattering by targets with significant contrast in terms of acoustic impedance, hardness, size, and/or shape can be expected to scatter ultrasound at higher intensities and over larger angles than from targets that form the background matrix. The differential response between objects with acoustic impedance contrast when compared to the surrounding medium is preferably achieved by control of composite ultrasonic sound fields. The composite sound fields are determined by the particular ultrasound transducer specifications as well as its fixed spatial configuration.

The fixed spatial configuration is defined by the angles 435, 436 (see FIG. 8A) the height of the transmitter, h, and the height of the receivers, l and l'. The heights h, l, and l' and the angles 435, 436 are relative to a coordinate system whose origin is in the vertical center of the process stream. The transmitter height, h, is set so that the center of the transducer's focal zone is positioned in the vertical region of about 0 to 0.25 R, where R is the radius of the process stream (or half the thickness of the stream in the case of a rectangular channel). The receiver heights, l, and l' are set so that the center of the transducer's focal zone is positioned in the vertical region of 0 to 0.25 R. The size of the focal zones are selected to span the thickness of channel 44 and the axes of the transmit beam and the receiver beams lie in the same vertical plane. In the illustrated embodiment, the heights h, l, and l' are each about equal to the focal length of the transducer.

The angles 435, 436 are in the range of 18 degrees to 162 degrees. Selection of optimum angles is dependent on the selected inspection frequency, the transducer focal length, and the size range of the foreign material sought to be detected in the process stream. The interrogation frequency to be employed can be determined empirically using a representative sample of the process stream medium containing no extraneous materials. Preferably a high frequency is used that does not result in root mean squared (RMS) variation of 0.5 or more across a representative portion of the process stream. A typical representative portion might be a lateral aperture of at least 10×D, where D is the dimension that approximates the graininess of the medium. The angles 435, 436 can then be determined empirically using a representative sample of the process stream medium containing a foreign object whose size and acoustic impedance is representative of foreign objects to be detected. The angles 435, 436 are preferably adjusted in the range of 18 degrees to 162 degrees until the scattered signal amplitude is at least 6 dB above RMS background signal.

It is expected that the optimum inspection frequency and angles will vary according to the process stream being inspected. It has been found that for a process stream of whole meat chicken breasts, a frequency of 1.0 MHz with the angles 435 and 436 between 18 degrees and 22 degrees provides acceptable results for a ¾ inch channel thickness (2R) and transducers with 2 inch focal lengths.

Figure 2:
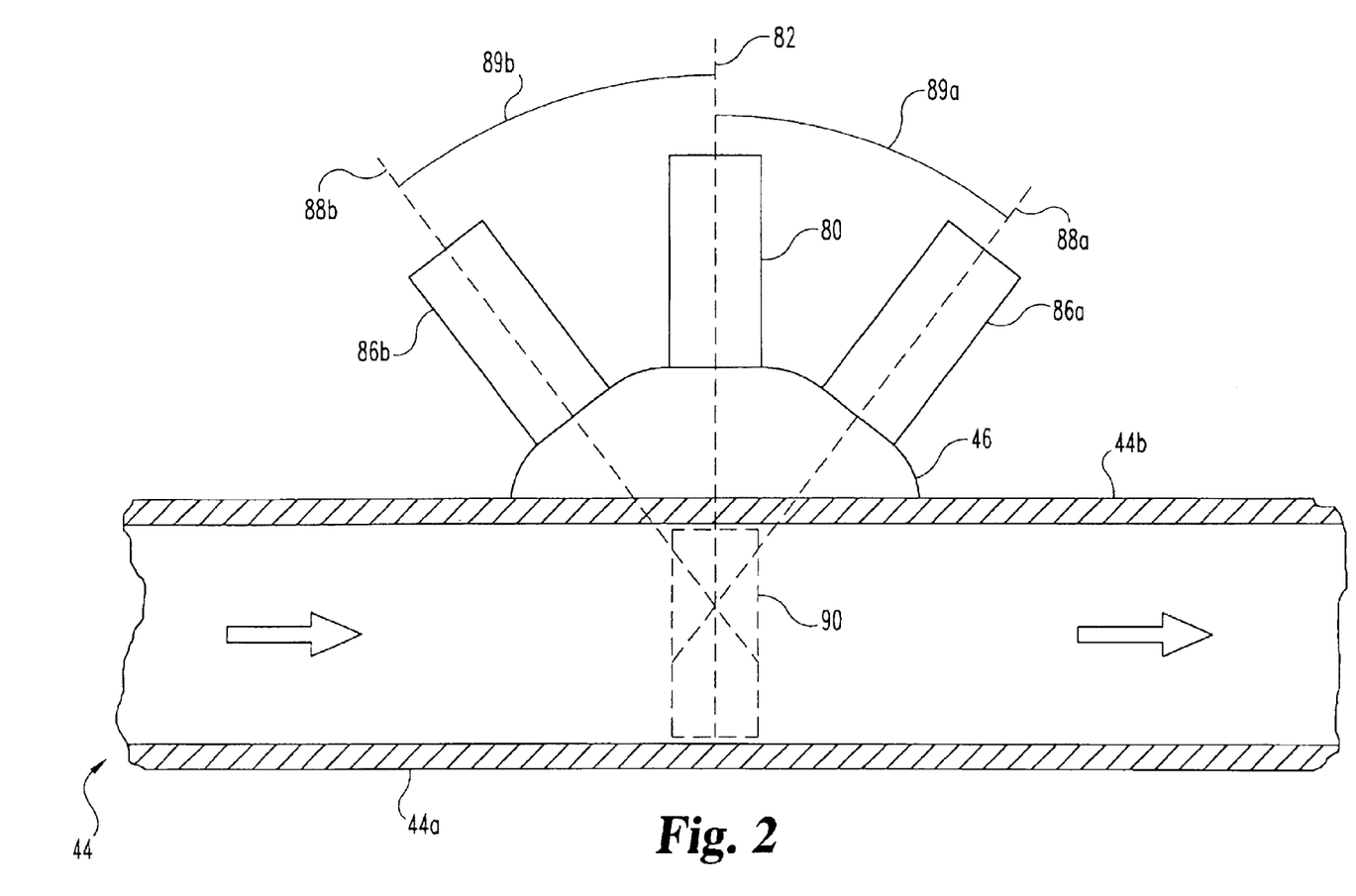
FIG. 2 is a side sectional view of an inspection station for the system of FIG. 1.

Turning now to FIG. 2, an alternative configuration for inspection station 440 is illustrated. It is to be understood that inspection station 40, like the all other inspection stations presented herein, can be used in place of station 440, with corresponding adjustment to signal processing based on any transmitter and receiver differences. Station 40 includes an ultrasound transmitter 80 and ultrasound receivers 86a and 86b. Transmitter 80 is aligned along an interrogation axis 82 to deliver ultrasound energy to an inspection zone 90 in the bulk material 33 contained in channel 44. Ultrasound receivers 86a and 86b are arranged to detect the off angle scattering of ultrasound from zone 90. Both transmitter 80 and receivers 86a and 86b are arranged above the closed channel 44 in contact with a solid acoustic couplant 46. In one mode of operation, a pulse of ultrasound from transmitter 80 travels through couplant 46 and the upper portion 44b of channel 44 before entering zone 90. Scattered ultrasound emanating from zone 90 then travels through portion 44b for detection by receivers 86a and 86b.

As depicted in FIG. 2, detector 86a is aligned along detection axis 88a and detector 86b is aligned along detection axis 88b. Axes 88a and 88b each intersect zone 90 and axis 82. Detector 86a is aligned at an angle 89a with respect to interrogation axis 82, and detector 86b is aligned at angle 89b. Each angle 89a or 89b defines a relationship between transmitter 80, zone 90, and receiver 86a or 86b and thus can range from zero to 180 degrees. While axes 88a and 88b each intersect axis 82 as illustrated, it is understood that one or more of the axes can be skewed relative to axis 82, the angles 89a and 89b then being defined by the intersecting projections of the skew axes.

Figure 3:
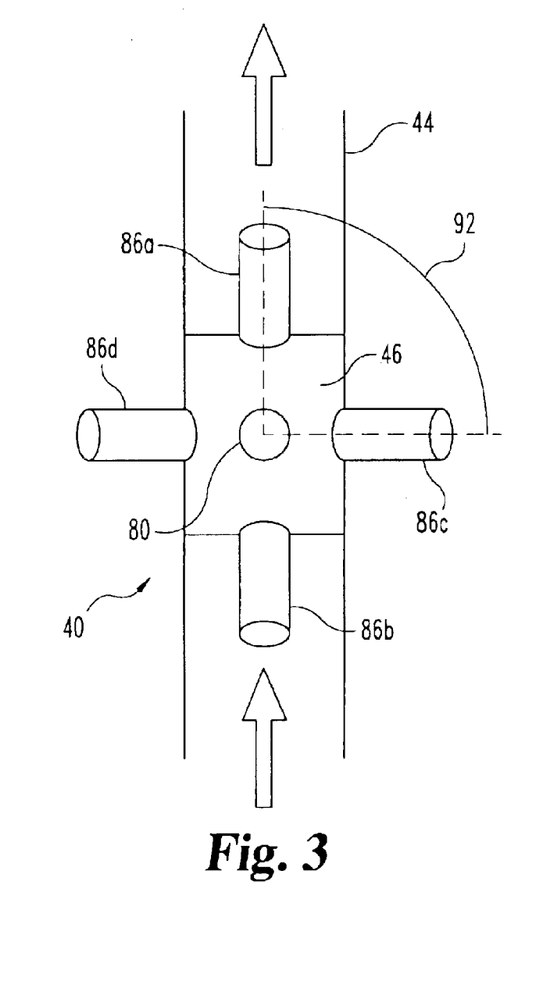
FIG. 3 is a top view of the FIG. 2 inspection station.

Turning now to FIG. 3 and with continued reference to FIG. 2, a top view of inspection station 40, looking down interrogation axis 82 is illustrated. Inspection station 40 includes additional detectors 86c and 86d aligned about ultrasound transmitter 80. Detectors 86a–86d are approximately equally spaced about interrogation axis 82 such that the angle 92 between the detection axes is about 90 degrees.

Figure 4:
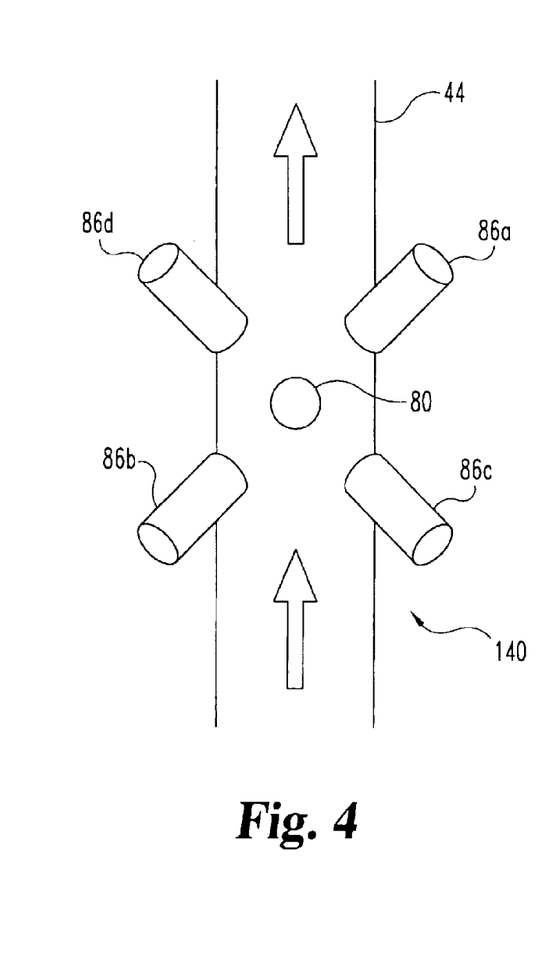
FIG. 4 is a top view of an alternative configuration for the inspection station of FIG. 2.

FIG. 4 depicts an alternative inspection station arrangement. Inspection station 140 is otherwise identical to station 40 save that each detector 86a–86d is rotated about 45 degrees about the interrogation axis 82. An appropriate acoustic coupling agent (not shown) is provided between channel 44 and each of transmitter 80 and receivers 86a–86d. Whereas in station 40 the detection axes had projections into the flow path that were approximately parallel or perpendicular to the bulk material flow (indicated by arrows), the detection axes in station 140 have projections that are at about 45 degree angles to the flow direction.

Figures 5, 6B:
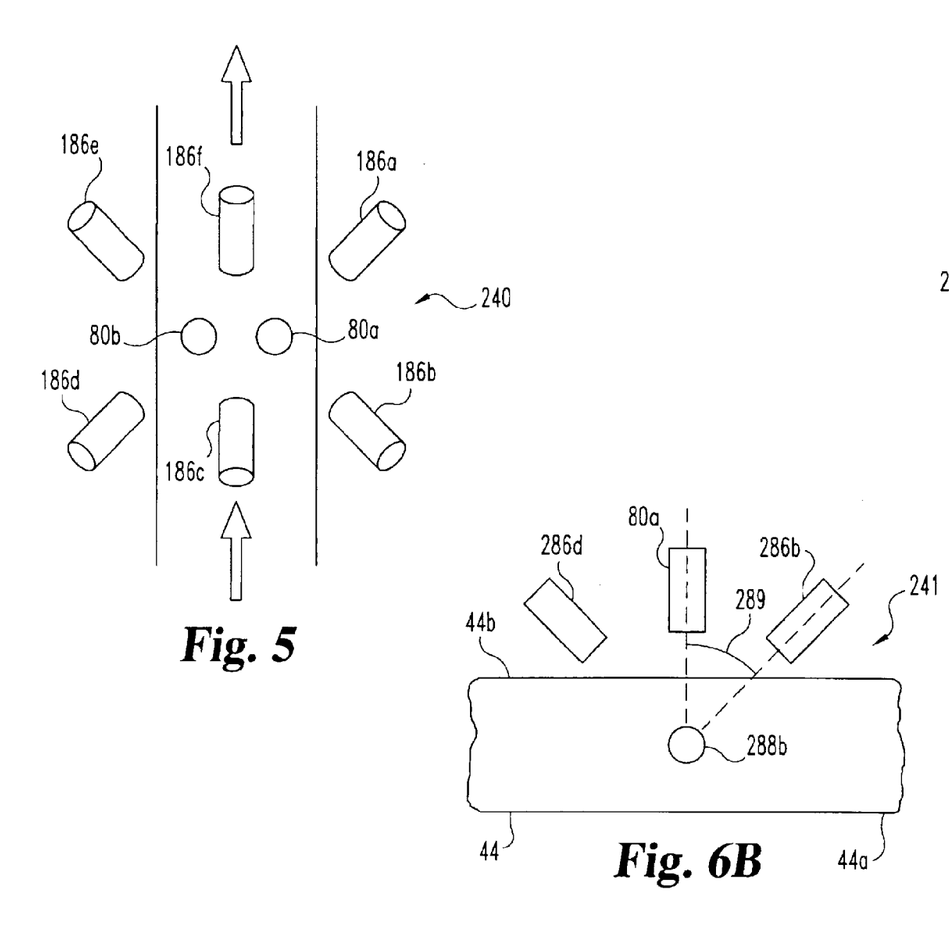
FIG. 5 is a top view of a further alternative configuration for an inspection station.
FIGS. 6A and 6B are top and side views respectively of still another alternative configuration for an inspection station.

Turning now to FIG. 5, a still further embodiment of an inspection station is depicted. Station 240, like station 140, can be used in place of station 40. Station 240 includes a pair of ultrasound transmitters 80a and 80b with parallel interrogation axes. Each of the interrogation axes of transmitters 80a and 80b are also aligned in a plane perpendicular to the flow direction the material in channel 44. A plurality of receivers 186a–186f are aligned around the transmitters with their detection axes at angles relative to the each of the interrogation axes. As described above, an appropriate acoustic coupling agent (not shown) is provided between channel 44 and each of the transmitters and receivers.

Figure 6A:
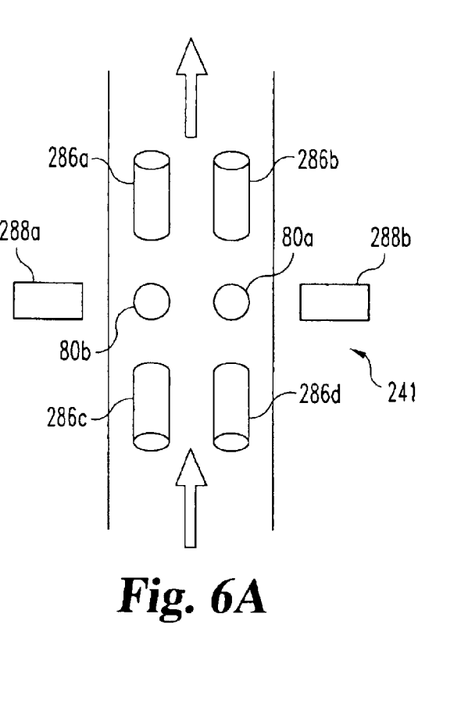

FIGS. 6A and 6B illustrate a still further embodiment of an inspection station. Like station 240, inspection station 241 includes multiple transmitters 80a and 80b surrounded by multiple receivers 286a–286d, 288a and 288b. Receivers 286a–286d are each above the top portion 44b of flow channel 44 and aligned at angle 289 relative to the interrogation axis. Angle 289 is, for example, approximately 45 degrees. Receivers 288a and 288b are at the sides of channel 44 with their detection axes at approximately a 90 degree angle to the interrogation axes.

Figure 7A:
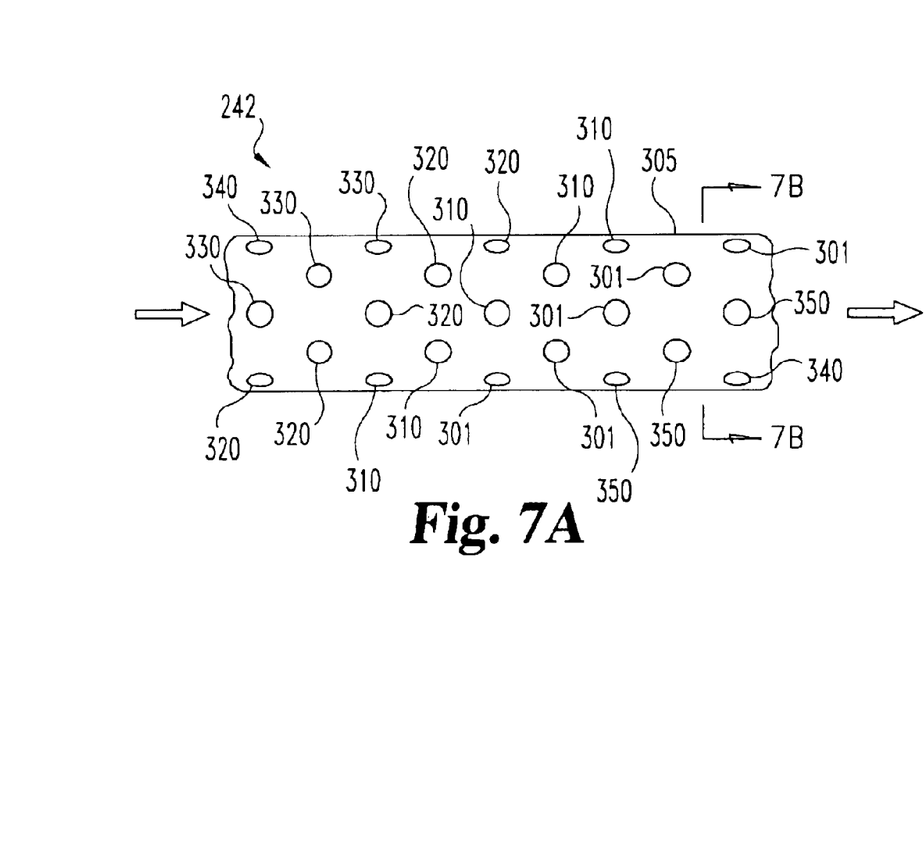
FIGS. 7A and 7B are side and sectional views respectively of yet another alternative configuration for an inspection station.
Figure 7B:
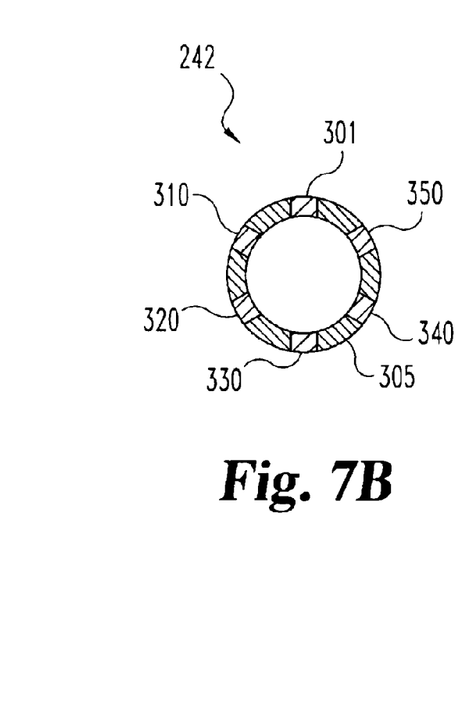

A still further variation of an inspection station is depicted in FIGS. 7A and 7B. Station 242 differs from the previous stations 40, 140, 240, 241, 440 in that the transmitter 301 and receivers 310, 320, 330, 340, 350, are formed integrally with the conduit 305 for carrying the bulk material 33. Each transmitter 301 includes associated receivers 310, 320, 330, 340, 350 forming a transmitter/receiver set in a common plane perpendicular to the flow direction. Several transmitter/receiver sets are located at spaced locations along the length of the conduit 305, with adjacent transmitters 301 at different angular positions about the flow direction to reduce the effect of any dead spots at any one transmitter/receiver set location.

The provision of successive transmitter/receiver sets at varying angular orientations can also be employed for any of the aforementioned inspection stations 40, 140, 240, 241, 242, 340. Inspection stations 40, 140, 240, 241, 242, 440 can also each be employed singly or in combination with one or more other inspection stations 40, 140, 240, 241, 242, 440. Furthermore, it is to be understood that each of the transmitters and receivers in stations 40, 140, 240, 241, 242 are preferably, though not essentially, either cylindrically or spherically focused as described above with respect to station 440.

One particular application of the present inventive techniques is to detect the presence of harder objects, such as bones or bone fragments, in a process stream. However it is contemplated that other scattering targets, for example a latex glove in a process stream of foodstuff or other material can be detected according to the principles of the present invention. A still more particular application is to detect the presence of foreign material in an highly heterogeneous process stream or one in which multiple diverse scattering targets are normally present.

A particular example of the detection of harder objects in a heterogeneous process stream is presented below with respect to the detection of bone in chicken meat. A typical process stream in the poultry application includes a slurry of liquid and chicken breasts. The interface between the breasts and the liquid is an ultrasound scattering surface, and inhomogeneities in the chicken breasts themselves, for example flesh features (filaments and bundles in the meat muscle), can be ultrasound scattering sources. However, bone is harder and has a different size and shape than the chicken breast or the carrying liquid and the scattering at a given off-angle attributable to bone is adequately detectable over the scattering at the same given off-angle attributable to the bulk chicken breast tissue or tissue liquid interfaces.

The exact angle of the detected off-angle scattering response optimally suited for any particular application will likely vary for different applications of the present invention. Nonetheless, it is expected that scattering angles of between 10 and 55 degrees will be useful for many applications of the present invention.

In addition, the selection of the inspection frequency can provide balance between needed scattering response to foreign material with minimized sensitivity to other benign structures in the bulk flow. In the chicken meat examples presented below, the inspection frequency of 1 MHz corresponds to a wavelength of about 1.5 mm in tissue. This wavelength is comparable with the longest length dimension for bone fragments of interest. Wavelength to target maximum dimension ratios are preferably between 0.5 and 5, and more preferably are at least one.

In carrying out the present invention, ultrasonic signals having a frequency in the range of about 0.1 to 50 MHz may be employed, with signals in the range of 0.1 to 5 MHz being preferred. For certain embodiments, it is desirable to have the ultrasonic wavelength within the described ratio limits of the size of the foreign object to be detected.

Further, when implementing the present invention in fixed relation to a moving material, for example detecting foreign material in a flowing process stream, it is desirable to sequentially and rapidly interrogate the material to increase the probability of foreign material detection. A signal pulse repetition rate may suitable be on the order of 30 to 850 pulses/second, with a range of 250 to 850 pulses/second being preferred for material flowing at a speed of about 30 cm/sec.

Various types of ultrasound transmitters and receivers are useful in practicing the present invention including both piezoelectric, electro-magnetic-acoustic transducers (EMAT), laser-ultrasound, and magnetoelectric transmitters and receivers. These may be obtained from conventional ultrasound suppliers such as Parametrics located in Boston, Mass. and Xactec located in Pasco, Wash.

A variety of cooked and uncooked foods may be inspected in accordance with the present invention, especially those in which water is present as a continuous phase constituting, for example at least about 30% or more by weight thereof. Non-limiting examples of foods suitable for inspection in accordance with the invention include, minced or strained baby foods, (e.g. meats, fruits, vegetables, and mixtures thereof), bologna, sausage fillings, liverwurst, frankfurter meat and the like, tomato ketchup, gruel, puddings, and soups. In addition, pitted or sectioned foods such as olives, peaches, pears, pineapple, prunes, and cherries, in whole or sliced form, suspended in a continuous liquid medium such as water, sugar syrup, or olive oil, may be inspected for the presence of pits, seeds and stems. Similarly, whole fruits and vegetables such as onions and potatoes may be immersed in a continuous liquid transport medium (such as water) and non-intrusively inspected for homogeneity, e.g., for the presence of rotten cores, embedded solids, or other internal abnormalities.

Advantageously, highly heterogeneous foodstuffs may also be inspected in accordance with the present invention. For example, inspection for unremoved pits in cherries suspended in water. In addition, plums, olives, pears and other whole and halved fruits may similarly be inspected. Although most preferably applied to human and animal foodstuffs (including beverages, e.g., milk, alcoholic beverages, and soft drinks), the apparatus and process of the present invention may advantageously be utilized to inspect a wide variety of other substances. In one preferred alternative embodiment, the inspected material will be a fluid, which can include a fluid suspension or slurry material. Thus, among the various materials which may be inspected are liquid, pasty, or highly viscous substances including without limitation petroleum products such as gasoline, motor oil, waxes and greases. Additional materials for inspection include various chemicals solvents, liquid household products, polymer streams, and the like.

It is to be understood that the present invention is applicable to a wide variety of processing environments. For example, in addition to the inspection of flowing or otherwise pumpable process streams, where conveyor assembly 38 is based on a pump and conduit, material carried on any other type of material conveyor can also be interrogated. Alternatively or in addition to use of the invention in conjunction with moving process streams, the invention is applicable for example to monitor a material in a batch process.

It should be further understood that the presence of foreign objects in a bulk material is only one property measurable in accordance with the present invention and that the present invention can be applied to measure other material properties. For example, the present invention can be used to quantify the degree of mixing in a fluid material by determining the nature or amount of inhomogeneity in the material. In this case, the relative amount of ultrasound off-angle scattering provides a measure of the degree of inhomogeneity in the material. Another application includes determining a material transition, such as the onset of crystallization or a change in average particle size in a suspension or slurry. In this application, a material can be substantially continuously monitored for a change in the off-angle scattering response, which change would be used to determine the onset or degree of transition.

Additional inspection of material in the process stream can also be utilized to supplement or complement the detection achieved according to the ultrasonic techniques described herein. Optical backlit information can be used with or without the ultrasound off-angle scattering data to determine the presence of foreign material in a process stream. It has been found that optical backlighting is particularly effective in detecting surface bones or bone fragments in meat. Is has also been found that the ultrasound scattering technique is particularly effective at detecting buried bones. Accordingly, in a preferred alternative embodiment, both the backlighting technique and the ultrasound scattering technique are used where the combination of the two techniques is surprisingly effective in detecting foreign material. Other complimentary methodologies such as X-ray, electromagnetic, or electrical impedance analysis can also be employed either alone or in combination with any of the techniques described herein.

Figure 10:
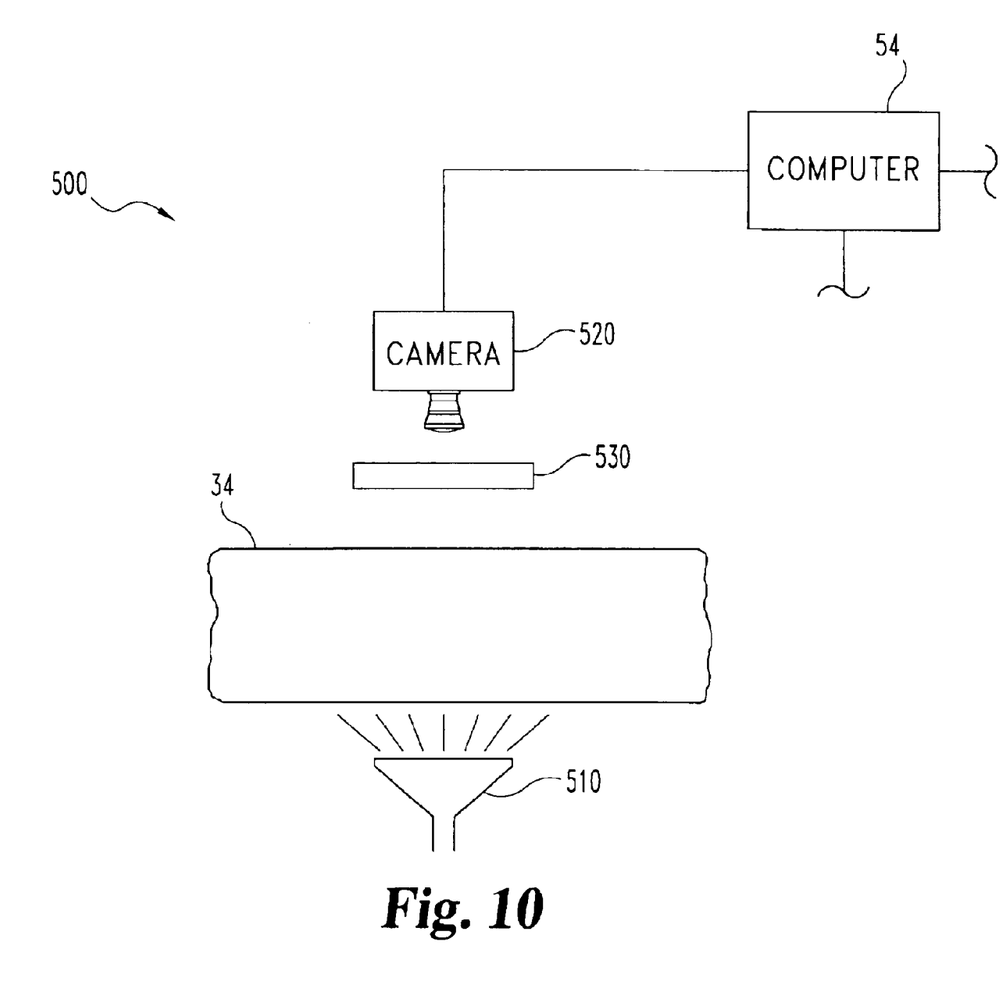
FIG. 10 is a schematic illustration of an optical backlighting system.

Turning now to FIG. 10, a schematic illustration of an optical inspection station 500 is depicted. In this optical inspection embodiment, computer 54 (or a plurality of computers in one or two way communication) receives the output of the optical inspection. In the chicken breast example, a portion 34 of the process stream upstream (or downstream) from station 440 is backlit with a light source 510. A suitable light source is a halogen lamp. A video camera 520 with a 550 nm bandpass filter 530 is then used to capture the image of the light that transmits through the chicken. It is to be understood that portion 34 of the process stream is constructed of appropriately transparent material.

Surprisingly, it has been found that light in the preferred 500–600 nm wavelength range gives a high contrast between meat and bone. A more preferred range for chicken bone inspection is 530–570 nm. Accordingly, computer 54, which preferably includes a frame grabber and processing instructions operable to processes captured backlit images of the chicken breast in real time, can readily determine the presence of bone. One method of computer determination is to perform threshold detection of the captured images, where the presence of a predetermined number of adjacent pixels in the captured image exceeding a threshold indicates the presence of bone. It is to be understood that a bone will show up as a shadow image and that, as used herein, exceeding a threshold includes both having a value numerically above a threshold value and having a value numerically below a threshold value. Alternatively or in addition a human operator can observe the backlight images to determine the presence of bone.

Figure 11:
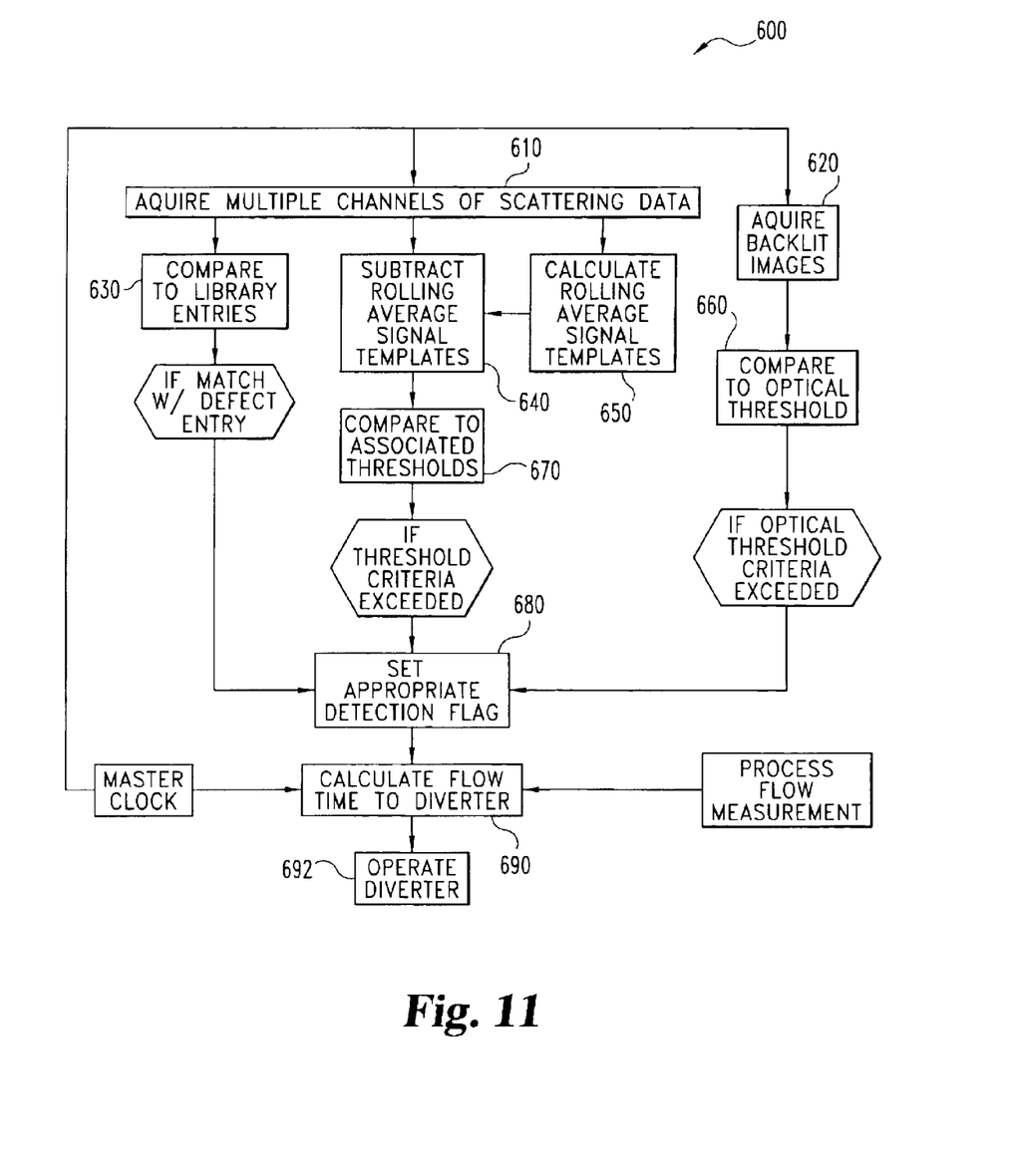
FIG. 11 is a flow chart of one embodiment of a process for detecting foreign material.

Turning now to FIG. 11, a flow chart of a combined ultrasound scattering-optical backlighting detection technique useful for determining the presence of foreign material in a process stream is illustrated. Process 600 begins with the acquisition of multiple channels of ultrasound scattering data in action 610. The multiple channels of data correspond to ultrasound receivers at fixed spatial locations along the process flow path and can be acquired by any of the systems and techniques described herein.

A rolling average of the signal templates for each channel of data is then calculated in action 650. The rolling average is representative of scattering from the bulk material in the process stream and is subtracted from the acquired scattering data in action 640, with the resulting signals compared to associated thresholds in action 670. If a threshold criteria is met, an appropriate detection flag is set in action 680. As described above, the threshold criteria can be one or more receivers trained on overlapping process flow volumes exceeding associated thresholds. Accordingly, the particular detection flag that is set will depend on the spatial location of the receiver or receivers which triggered the flag. In action 690 information regarding the process flow rate and the overall time are used to calculate an appropriate delay, and a diversion valve is operated in action 692 to remove the foreign material from the process stream.

The scattering data are also compared to a library of entries in action 630. The library contains entries corresponding to scattering signals from known occurrences of foreign material in the process stream. Upon finding a substantial match, for example with a trained neural network, a detection flag is set in action 680, a delay is calculate in action 690, and the diversion valve is operated in action 692.

Concurrently with the acquisition of scattering data in action 610, backlit images of the process stream are acquired in action 620. These backlit images are acquired by any of the system or techniques described herein or by any means know in the art. Most preferably, the backlit images include light in a wavelength range that achieves a high degree of contrast in the flow stream, which for detecting bone in chicken meat is between about 500–600 nm. The images are captured and digitized for comparison of one or more portions of the image to associated thresholds. If the threshold criteria is met, an appropriate detection flag is set in action 680. The optical detection flag reflects not only the spatial location of the optical inspection station, but also the spatial location within a captured image, recognizing that a single image can include a large area of the process stream. The flow time for the optically detected foreign material is calculated in step 690, and the diversion valve is operated in action 692.

In one variation of the technique, the rolling average of the ultrasound signals calculated in step 650 excludes any signals determined to represent foreign material. This can be accomplished by calculating the rolling average with signals that do not meet threshold criteria. In another variation, signals that are found to meet threshold criteria are added to the library to thereby expand the library under operating conditions.

EXAMPLE

The inspection station depicted in FIGS. 8A and 8B was used to detect bones in chicken breast, where water was used in place of wedge 446 to couple sound into and out of the channel. A packed chicken breast slurry was contained in a channel six inches wide and ¾ inch high and traveled at a speed of 15 inches/second. Eight cylindrically focused ultrasound receivers were positioned around a pair of central longitudinally extending and cylindrically focused transmitters where the relative angle between transmitter axis and receiver axis was between about 18 and 22 degrees. The focal depth of all transducers was 2 inches and the transmitter operated at a 1 MHz inspection frequency. Using threshold amplitude detection and the requirement for more than one receiver to exceed the threshold, over 90% of manually inserted chicken bones of various types and sizes were detected.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. All publications, patents, and patent applications cited in this specification are herein incorporated by reference as if each individual publication, patent, or patent application were specifically and individually indicated to be incorporated by reference and set forth in its entirety herein.

What is claimed is:

1. A method, comprising:
   interrogating a process stream with ultrasound by pulsing a focused sound field of ultrasound into the process stream,
   receiving an off-angle ultrasound scattering response to the interrogating with a plurality of detectors at spaced location; and determining presence of foreign material in the process stream if the off-angle ultrasound scattering response exceeds a predetermined threshold.

2. The method of claim 1 wherein the process stream is interrogated with ultrasound from an ultrasound transmitter aligned along an interrogation axis and wherein the received ultrasound response scatters at an angle of greater than 10 degrees from the interrogation axis.

3. The method of claim 2 wherein the received ultrasound response scatters at an angle of between about 10 and about 45 degrees from the interrogation axis.

4. The method of claim 2 further comprising determining the spatial location of the foreign material in the process stream based on the response from detectors focused on different portions of the process stream.

5. The method of claim 4 wherein the scattering response is received by at least one ultrasound receiver aligned along a detection axis non-parallel to the interrogation axis and the angle between the interrogation and detection axes is between about 15 and about 25 degrees.

6. The method of claim 1 wherein the process stream is heterogeneous and the foreign material is contained in the heterogeneous process stream, and wherein the predetermined threshold is selected to exceed the off-angle scattering response attributable to scattering targets of the heterogeneous process stream when devoid of foreign material.

7. The method of claim 1 wherein the process stream is interrogated with ultrasound at a frequency of between about 0.1 and 5 MHz in air.

8. The method of claim 1 wherein the process stream is interrogated with ultrasound with a wavelength in the process stream and the detected foreign material has a length dimension, and wherein the length dimension divided by the wavelength is greater than about one.

9. The method of claim 1 further comprising operating a diverter to select a diversion channel for at least a portion of the process stream when presence of foreign material is determined.

10. The method of claim 1 wherein the process stream is contained in a conduit having at least one flat wall and the process stream is interrogated with ultrasound through the flat wall.

11. The method of claim 10 wherein the plurality of detectors receive the off-angle scattering response through the flat wall.

12. The method of claim 11 wherein the conduit defines a flow path with a generally rectangular cross section adjacent the detectors.

13. The method of claim 1 wherein the process stream is contained in a conduit defined by at least one wall and the interrogating ultrasound and the received off-angle scattered ultrasound pass through a solid acoustic coupling in contact with the at least one wall.

14. The method of claim 1 further comprising comparing the response from the plurality of detectors to associated predetermined thresholds, wherein the presence of an foreign material in the process stream is determined when the received off-angle ultrasound scattering response for more than one of the plurality of detectors exceeds the associated predetermined thresholds.

15. A system, comprising:
a conveyor operable to provide a process stream;
one or more inspection devices operable to transmit pulses of focused ultrasound to interrogate the process stream and receive an off-angle ultrasound scattering response to interrogation with the ultrasound; and
a processing device operable to determine presence of a foreign material in the process stream based on a comparison of the off-angle ultrasound scattering response to a predetermined threshold;
wherein the inspection devices include a plurality of spaced receivers each operable to receive an off-angle ultrasound scattering response to interrogation with ultrasound from a common transmitter.

16. The system of claim 15 wherein the processing device is operable to compare the received scattering response from each of the receivers to predetermined associated thresholds.

17. The system of claim 15 wherein the receivers are focused on different portions of the process stream and the processing device is operable to provide an indication of the spatial location of the foreign material in the process stream.

18. The system of claim 15 wherein the processing device is operable to compare the received scattering response from each of the receivers to associated predetermined background response levels.

19. The system of claim 15 wherein the one or more inspection devices include an ultrasound transmitter operable to deliver a cylindrically focused sound field to the process stream with the focal line generally perpendicular to the flow direction of the process stream.

20. The system of claim 19 wherein the plurality of receivers are positioned in a line generally parallel to the focal line of the cylindrically focused sound field.

21. The system of claim 15 wherein the process stream has at least first and second paths downstream from the one or more inspection devices, the system further comprising a diverter operable to cause at least a portion of the process stream to travel down the second path when the presence of an foreign object in the process stream is determined.

22. The system of claim 15 wherein the process stream is contained in a conduit having at least one flat wall and the process stream is interrogated with ultrasound through the flat wall.

23. The system of claim 22 wherein the plurality of spaced receivers receive the off-angle scattering response through the flat wall.

24. The system of claim 23 wherein the conduit defines a generally rectangular cross section.

25. The system of claim 15 wherein the process stream is contained in a conduit defined by at least one wall and the interrogating ultrasound and the received off-angle scattering response pass through a solid acoustic coupling in contact with the at least one wall.

26. The system of claim 25 wherein the conduit defines a bulk flow direction and wherein the solid acoustic coupling is a wedge piece defining a face parallel to the bulk flow direction for receiving an inspection device for transmitting acoustic pulses and a pair of faces not parallel to the flow direction for receiving inspection devices for receiving the scattering response.

27. A method, comprising:
interrogating a stream of foodstuff with ultrasound;
detecting an off-angle ultrasound scattering response to said interrogating with a plurality of spaced ultrasound receivers; and
determining if foreign material is present in the foodstuff based on the off-angle ultrasound scattering response.

28. The method of claim 27 wherein the foodstuff is meat and the foreign material is bone.

29. The method of claim 27 wherein the interrogation includes pulsing a focused sound field of ultrasound into the stream of foodstuff, the focused sound field spanning a majority of the cross section of the stream of foodstuff such that a majority of the material in the stream of foodstuff can pass through the focused sound field.

30. The method of claim 29 wherein the plurality of receivers include at least two receivers focused on overlapping volumes.

31. The method of claim 29 wherein the plurality of receivers include at least two receivers focused on substantially non-overlapping volumes.

32. The method of claim 31 wherein the plurality of receivers include at least two receivers focused on overlapping volumes.

33. The method of claim 32 further comprising operating a diverter downstream from the receivers to selectively divert a portion of the stream of foodstuff.

34. The method of claim 29 wherein the foodstuff is interrogated with ultrasound from an ultrasound transmitter aligned along an interrogation axis and wherein the received ultrasound response scatters at an angle of between about 10 and 35 degrees from the interrogation axis.

35. A system comprising:
a conduit having at least one flat wall operable to receive a process stream,
one or more inspection devices operable to transmit ultrasound through the flat wall to interrogate the process stream,
a plurality of spaced receivers each operable to receive an off-angle ultrasound scattering response to interrogation with the ultrasound; and
a processing device operable to determine presence of a foreign material in the process stream based on a comparison of the off-angle ultrasound scattering response to a predetermined threshold.

36. The system of claim 35 wherein the plurality of receivers are operable to receive the off-angle ultrasound scattering response through the flat wall.

37. The system of claim 35 wherein the one or more inspection devices includes a cylindrically focused ultrasound transmitter.

38. The system of claim 37 wherein the conduit defines a bulk flow direction adjacent the one or more inspection devices and the focal line of the transmitter is substantially perpendicular to the bulk flow direction.

39. The system of claim 35 wherein the conduit defines a flow path with a generally rectangular cross section adjacent the one or more inspection devices.

40. The system of claim 39 further comprising a process stream of foodstuff in the flow path.

41. A system comprising:
a conduit defining a flow path having a portion with a generally rectangular cross section,
one or more inspection devices operable to transmit ultrasound to interrogate a process stream in the generally rectangular portion of the flow path,
a plurality of spaced receivers each operable to receive an off-angle ultrasound scattering response to interrogation with the ultrasound; and
a processing device operable to determine presence of a foreign material in the process stream based on a comparison of the off-angle ultrasound scattering response to a predetermined threshold.

42. The system of claim 41 wherein the one or more inspection devices are operable to transmit pulses of focused ultrasound into the flow path.

43. The system of claim 41 wherein the plurality of receivers include at least two receivers focused on overlapping volumes.

44. The system of claim 41 wherein the plurality of receivers include at least two receivers focused on substantially non-overlapping volumes and the processing device is operable to provide an indication of the spatial location of the foreign material in the process stream.

45. The system of claim 44 wherein the plurality of receivers include at least two receivers focused on overlapping volumes.

46. The system of claim 45 wherein an acoustic path is between the inspection device and the process stream and between the process stream and the receivers and solid material forms a majority of the acoustic path.

47. The system of claim 46 wherein the flow path defines a bulk flow direction and the solid material defines a face parallel to the bulk flow direction in contact with the one or more inspection devices and a pair of faces not parallel to the flow direction in contact with the receivers.

48. The system of claim 46 wherein the solid material is integral with the conduit.

49. A system comprising:
a conduit operable to receive a process stream,
one or more inspection devices operable to interrogate a volume of material in the process stream with ultrasound,
at least two receivers focused on substantially non-overlapping interrogated volumes of material each operable to receive an off-angle ultrasound scattering response to the interrogation; and
a processing device operable to determine presence of a foreign material in the process stream and to provide an indication of the spatial location of the foreign material in the process stream based on a comparison of the off-angle ultrasound scattering response of each receiver to a predetermined threshold.

50. The system of claim 49 wherein the one or more inspection devices are operable to transmit pulses of focused ultrasound into the process stream.

51. The system of claim 49 wherein there are at least two receivers focused on overlapping volumes.

52. The system of claim 49 wherein an acoustic path is between the inspection device and the process stream and between the process stream and the receivers and solid material forms a majority of the acoustic path.

53. The system of claim 52 wherein the conduit defines a bulk flow direction and the solid material defines a face parallel to the bulk flow direction in contact with the one or more inspection devices and a pair of faces not parallel to the flow direction in contact with the receivers.

54. The system of claim 53 wherein the solid material is integral with the conduit.

55. The system of claim 26 wherein the wedge piece and the at least one wall are integral.

56. The method of claim 1 further comprising:
capturing an image of the process stream while optically backlighting the process stream;
determining presence of foreign material in the process stream if at least a portion of the captured image exceeds a predetermined threshold.

57. The method of claim 28 further comprising:
capturing an image of the foodstuff stream while optically backlighting the stream;
determining presence of bone in meat if at least a portion of the captured image exceeds a predetermined threshold.

58. The method of claim 57 wherein the captured image includes light in the range of between about 500 and about 600 mm.

* * * * *